United States Patent [19]

Carlsen et al.

[11] Patent Number: 5,506,678
[45] Date of Patent: Apr. 9, 1996

[54] SYSTEM FOR COLLECTING WEAKLY SCATTERED ELECTROMAGNETIC RADIATION

[75] Inventors: William F. Carlsen, Woodside; Tad D. Simons, Palo Alto; Richard J. Pittaro, San Carlos; George W. Hopkins, II, Sunnyvale; Damien F. Gray, Mountain Veiw, all of Calif.

[73] Assignee: Hewlett Packard Company, Palo Alto, Calif.

[21] Appl. No.: 840,108

[22] Filed: Feb. 24, 1992

[51] Int. Cl.$^6$ ............................. G01N 21/00; G01J 31/44
[52] U.S. Cl. ............................................. 356/338; 356/301
[58] Field of Search ..................................... 356/335–343, 356/301, 236, 246, 319; 250/222.2, 228, 574

[56] References Cited

U.S. PATENT DOCUMENTS

| | | | |
|---|---|---|---|
| 3,406,289 | 10/1968 | Schleusener | 356/335 |
| 3,414,354 | 12/1968 | Siegler, Jr. . | |
| 3,556,659 | 1/1971 | Hawes . | |
| 3,704,951 | 12/1972 | Chupp | 356/75 |
| 3,723,007 | 3/1973 | Leonard | 356/75 |
| 3,766,489 | 10/1973 | Rosenberg et al. | 356/246 |
| 3,951,526 | 4/1976 | Grossman . | |
| 4,127,329 | 11/1978 | Chang et al. . | |
| 4,212,539 | 7/1980 | Berber et al. | 356/336 |
| 4,410,271 | 10/1983 | Matthews . | |
| 4,571,079 | 2/1986 | Knollenberg | 356/336 |
| 4,630,923 | 12/1986 | Tans | 356/301 |
| 4,645,340 | 2/1987 | Graham et al. | 356/301 |
| 4,648,714 | 3/1987 | Benner et al. | 356/301 |
| 4,676,639 | 6/1987 | Wagenen | 356/246 |
| 4,784,486 | 11/1988 | Van Wagenen | 356/301 |
| 4,818,882 | 4/1989 | Nexo et al. | 250/343 |
| 5,121,988 | 6/1992 | Blesener et al. | 356/442 |

FOREIGN PATENT DOCUMENTS

| | | |
|---|---|---|
| 1291535 | 10/1965 | Germany . |
| 1900885 | 1/1969 | Germany . |
| 2723939 | 7/1978 | Germany . |
| 1124126 | 3/1966 | United Kingdom . |
| 1171689 | 4/1967 | United Kingdom . |
| 88/00126 | 2/1988 | United Kingdom . |
| 2241080 | 8/1991 | United Kingdom ................... 356/301 |

OTHER PUBLICATIONS

English Translation of Ref. #DE2723939C2.
Printed advertisement for the RASCAL Gas Monitoring System by Albion Instruments of Salt Lake City, Utah.
"Low–Power Quasi–cw Ram an Oscillator" by E. P. Ippen, published in Allied Physics Letters, vo. 16, No. 8, Apr. 15, 1970 pp. 303–305.
"Intensification of Spontaneous Raman Spectra by Use of Hollow Core Optical Fibers": by G. E. Walrafen & J. Stone, published in Applied Spectroscopy, vol. 26, No. 6, Nov. 6, 1972, p. 303.

(List continued on next page.)

*Primary Examiner*—Hoa Q. Pham

[57] ABSTRACT

A System for Collecting Weakly Scattered Electromagnetic Radiation is disclosed. The present invention overcomes problems suffered by previous collection systems by providing a reliable and efficient device for intensifying and collecting the scattered radiation generated by laser induced scattering. The present invention employs a laser source which illuminates an unknown gas contained by a long hollow tube having a highly reflective sheathing. The illuminating electromagnetic radiation from the laser is directed along the entire length of the tube and collides with the molecules of the unknown gas in the tube. The collisions cause the emission of weakly scattered electromagnetic radiation that is shifted in reference to the illuminating radiation. The sheathing is sufficiently reflective of the scattered radiation to substantially contain it. An exit is coupled to the long hollow tube in such a way that the scattered radiation may pass from the reflective sheathing and be collected for analysis. The scattered radiation that is collected may be used in conjunction with conventional spectrometry devices to provide a reliable and rapid determination of the composition and concentration of a wide range unknown gasses. The system may also be used to analyze a wide range of other scattering medium.

4 Claims, 12 Drawing Sheets

OTHER PUBLICATIONS

"Liquid Core Optical Fibers in Raman Spectroscopy" by H. B. Ross & W. M. McClain, published in applied Spectroscopy, vol. 35, No. 4, 1981, pp. 439–442.

"Versatile, Efficient Ram an Sampling with Fiber Optics": by S. B. Schwab & R. L. McCreery, published in Analytical Chemistry, bolume 56, No. 12, Oct. 1984, p. 2199–2204.

"Remote, Long–Path length Cell for High–Sensitivity Raman Spectroscopy" by S. B. Schwab and R. L. McCreery, published in Applied Spectroscopy, vol. 41, No. 1, 1987, pp. 126–130.

"High–Resolution Raman Spectroscopy of Gases with cw–Laser Excitation" by A. Webber & J. Barrett, published in the Journal of the Optical Society of America, vol. 57, No. 1.

"An Efficient Intracavity Laser Raman Spectrometer" by M. Hercher et al, published in Applied Spectroscopy, vol. 32.

SYSTEM FOR COLLECTING WEAKLY SCATTERED ELECTROMAGNETIC RADIATION

BACKGROUND OF THE INVENTION

The present invention is a method and apparatus for enhancing the collection of weakly scattered electromagnetic radiation. More particularly the present invention is a device for intensifying and collecting the scattered radiation which is generated by laser-induced Raman scattering. The present invention may be used in conjunction with conventional spectrometric devices to perform molecular gas analysis in a variety of applications.

The designers of detection and monitoring instruments face numerous challenges in detecting the presence and concentration of both known and unknown substances. Many industrial sites can pose serious health hazards to workers due to the concentration of harmful fumes that are emitted by open tanks of cleaners or solvents, plating bath, or paint spraying equipment. One of the greatest perils posed by underground mining operations is the unexpected accumulation of potentially lethal gases. During a surgical operation, patients are anesthetized through the careful administration of gases such as nitrous oxide. The supply of these anesthetics must be regulated with great precision. In addition, the gases expelled in the breath need to be monitored continuously to determine the condition of the patient. Insuring the safety of persons situated in these diverse environments can require the constant monitoring of the substances in the air in which they breathe.

One instrument that is currently employed to detect the presence and concentration of various gases utilizes the physical phenomenon called Raman scattering. The instrument includes a laser which is directed toward a sample of gas contained in a chamber. The laser produces an intense stimulating beam of substantially monochromatic electromagnetic radiation, a small fraction of which is Raman scattered by the constituent gas molecules. This weakly scattered electromagnetic radiation exhibits a change or shift in frequency from that of the stimulating radiation. This change depends on the type of constituent gas which scattered the stimulating radiation, each gas generally having unique spectrum of frequency shifts. By measuring and interpreting the frequencies and intensities of the scattered radiation, the presence and concentration of the various constituent gasses in the sample can be deduced.

At the center of this system is the Raman scattering phenomenon which produces scattered radiation of a very weak intensity. There has been a long felt need to improve the efficiency and lower the cost of Raman scattering based instruments, but progress has been hindered by the weak intensity of the scattered radiation. Efforts to increase the intensity of the scattered radiation that is detected depends upon improving one or more of the following five factors:

1. the Raman molecular scattering cross-section;
2. the number density of the molecules distributed along the path of the stimulating radiation;
3. the intensity of the beam of stimulating radiation which scatters off the contained gasses;
4. the size of the solid angle in which the scattered radiation is collected;
5. the path length over which the beam interacts with the gas molecules;

Factor 1 Improvements

A Factor 1 improvement involves increasing the Raman molecular scattering cross-section. The Raman scattering cross-section is a measure of how much electromagnetic radiation is scattered per unit molecule. It is based largely on the geometry and quantum mechanics of the scattering molecule; these aspects being essentially fixed for any given molecule in the absence of an external electric or magnetic field. Changes induced in gas molecules by small external electric or magnetic fields generally produce only negligible increases in the Raman molecular scattering cross section. The changes induced in gas molecules by large external electric or magnetic fields often include unwanted chemical changes in the sample.

Factor 2 Improvements

A factor 2 improvement involves an increase in the number density of the molecules distributed along the path of the stimulating beam. This could be done, for example, by increasing the gas pressure in the sample cell. This usually involves a significant increase in the complexity and cost of the apparatus.

Factor 3 Improvements

A Factor 3 improvement involves an increase in the intensity of the stimulating radiation. This can be accomplished in part by using a laser as the source of stimulating radiation over using a less intense source. Increasing the power of a single laser or combining the beams of multiple lasers give further improvement, but this usually involves a significant increase in the complexity and cost of the system. It should also be considered that if the intensity of the beam reaches a sufficiently high level, it may induce unwanted chemical changes in the sample.

Factor 4 Improvements

A Factor 4 improvement involves the increase of the collection solid angle. This solid angle is a cone-shaped volume in which the scattered radiation is collected. This cone shaped volume begins at the cone's flat-topped apex which is defined by the collision area where the beam of stimulating radiation contacts the molecules. The cone shaped volume extends down to the cone's base defined by the entrance pupil of the device's collection optics.

In conventional devices, a laser beam is brought to a focus in the medium of interest, creating a minute region where the stimulating radiation interacts with molecules of the gas sample. Scattered radiation is then collected from this region with the collection optics. The collection optics are chosen to image the scattered radiation optimally into subsequent optical system elements such as filters, monochromators, and detectors. Generally, these elements have certain requirements for radiation input area and solid angle. In all imaging systems, the product of image area times solid angle (this product is called the étendue) is invariant at any point in the system. Image size and solid angle can be changed by various optical elements, but one is traded for the other.

Therefore, increasing the collection solid angle for a constant size illumination region is limited by the étendue of system optical elements such as filters, monochromators, and detectors. For example, filters generally have a small solid angle input requirement. Increasing the collection solid angle would require larger filters and increase the size and cost of the instrument.

Factor 5 Improvements

A Factor 5 improvement is the increase in the effective path length that is traversed by the stimulating radiation and observed by the collection optics. In general, an increase in the path length is limited by the area where the collection optics are focused. Thus an increase in the path length is generally limited by the étendue, as in the increase in the collection solid angle discussed above.

Raman Path Length in Hollow Glass Fibers

In their paper entitled "Intensification of Spontaneous Raman Spectra by Use of Hollow Core Optical Fibers" (Applied Spectroscopy, Volume 26, No. 6, Nov. 6, 1972, p. 585–589), Walrafen and Stone describe a system that analyzes a liquid benzene sample. The liquid sample is used as a scattering medium and analyzed by Raman scattering, using the liquid sample as a scattering medium. The system utilizes a hollow fused quartz glass fiber that is filled with the liquid sample. Stimulating radiation from an argon ion laser travels through the liquid sample so as to produce scattered radiation. The system collects a portion of the scattered radiation that travels through the liquid benzene core and reaches the collection optics at the end of the glass fiber. In general, scattered radiation that encounters the glass fiber is not collected unless it reflects back into the liquid core. For a given solid angle of collection, the path length is increased, while not increasing the étendue of the collection optics.

The range of samples that can be analyzed in such a system is limited because the system described by Walrafen and Stone utilizes the phenomenon of total internal reflection and requires a sample with a refractive index that is larger than the refractive index of the quartz material of the hollow fiber. Some liquids have a relatively high refractive index and may be analyzed in such a system. In general, gas samples have a refractive index that is much lower than that of the quartz material in the fiber wall. This means that such gas samples may not be analyzed by such a system unless they are somehow dissolved or incorporated into a high refractive index scattering medium. This may require a much more complex and expensive apparatus. It may also be significantly more difficult than analyzing the gas sample directly, due to interferences from the high refractive index scattering medium. This highlights the need for a system that increases the intensity of the scattered radiation while allowing for the direct analysis of a wide range of samples independent of the refractive index of the scattering medium.

Total Internal Reflection in Hollow Glass Fibers

In the hollow glass fiber system described by Walrafen and Stone, scattered radiation traveling in the liquid encounters the glass fiber at an angle of incidence. Walrafen and Stone adopt a convention of measuring the angle of incidence from a tangent to an interface between the liquid material and the glass material, rather than from a normal to the interface between the liquid material and the glass material. For the sake of clarity, all subsequent discussions will adopt the convention of measuring the angle of incidence from the tangent to the interface between the two materials.

The phenomenon of total internal reflection occurs when radiation travels through the high refractive index medium and encounters the lower refractive index glass wall at an incident angle less than a critical angle $\Theta_c$. Walrafen and Stone utilize a hollow glass fiber with quartz walls having a refractive index $n_c$. The hollow fiber is filled with a liquid benzene scattering medium having a refractive index $n_l$. Since $n_l$ is greater than $n_c$, the quantity $n_c/n_l$ is always less than 1. Walrafen and Stone use a laser beam with a wavelength of 488 nanometers as the stimulating radiation. The corresponding value for the refractive index of the quartz is given as approximately $n_c=1.463$. Standard chemical reference texts indicate that a corresponding value for the refractive index of the benzene at the wavelengths of interest is near an approximate value of $n_l=1.5$. The critical angle is then given by the equation:

$$\Theta_c = \text{Arccos}(n_c/n_l)$$

Computing the critical angle using $n_c=1.463$ and $n_l=1.5$ and the above formula gives a value for $\Theta_c$ of approximately 12.8 degrees. This means that there is total internal reflection for scattered radiation which travels in the liquid and grazes the glass wall at angles less than or equal to approximately 12.8 degrees.

In general, the glass fiber system operates by the total internal reflection of scattered radiation that is traveling in the liquid scattering medium and that encounters the wall at an angle that is less than the critical angle. In general, when scattered radiation encounters the wall at an angle that is greater than the critical angle, most of the scattered radiation refracts into the glass walls of the capillary optical fiber and very little is reflected. When the scattered radiation is nearly normal to the glass wall, the reflection is quite small. Though there is some small reflection at incident angles in the range between the normal and $\Theta_c$, the operation of the system relies primarily upon the phenomenon of total internal reflection wherein scattered radiation travels in the scattering medium and encounters the glass wall at angles less than $\Theta_c$.

The hollow glass fiber system described by Walrafen and Stone can also be understood in terms of electromagnetic theory rather than optical theory. The optical theory of refractive index is included in a more encompassing electromagnetic theory of complex impedance. The ratio of the refractive index of the glass to the refractive index of the scattering medium is equal to the ratio of the characteristic impedance of the scattering medium to the characteristic impedance of the glass. Because the characteristic impedance of the quartz glass and the characteristic impedance of the benzene are both real and are both about the same magnitude at the frequencies of interest, the difference between the two respective impedances is small and real. This means that there is in general a good impedance match between the two materials and there will be only a small reflection when electromagnetic radiation traveling in the benzene is incident normal to the glass. In general the glass is highly transmissive and little of the incident normal radiation will be contained by the glass. When electromagnetic radiation traveling in a first medium is not incident normal to a second medium, the radiation is incident to the second medium at an acute angle, and analysis of the system can not be reduced to simply an analysis of the respective characteristic impedances of the first and second mediums. Instead, the system is analyzed in terms of the characteristic impedance of the first medium and the load impedance presented by the second medium. When electromagnetic radiation traveling in the first medium is incident upon the second medium at a particular acute angle, the load impedance presented by the second medium varies with the measure of the particular acute angle. In this way, the load impedance is transformed so as to have real and imaginary components that are related to the measure of the acute angle.

For scattered radiation incident at acute angles less than the critical angle discussed above, the load impedance that the quartz glass presents to such scattered radiation is transformed to be purely imaginary. However, the benzene has a characteristic impedance that is purely real. This means that for acute angles less than the critical angle, there is a perfect impedance mismatch between the purely real characteristic impedance of the benzene and the purely imaginary load impedance presented by the glass. This perfect impedance mismatch results in the total internal reflection of such incident radiation. A discussion of purely imaginary load impedance and total internal reflection can be found in standard electromagnetics textbooks such as Ramo, Winery, and Van Duzer, "Fields and Waves in Communications Electronics" John Wiley & Sons (1965), Pages 362–363.

All the discussions above focus on reflection at the interface between the liquid core and the inner wall of the glass capillary. Walrafen and Stone do not focus their discussion on contributions due to reflection at the outer glass wall boundary, though such reflection should receive some consideration. Special attention should be given to the collection end of the capillary tube where the outer walls of the .capillary tube are shown as being immersed in the liquid benzene. Since the refractive index of the benzene is higher than the refractive index of the glass at the outer wall, and since there is only a small difference in the respective magnitudes of the two refractive indices, Walrafen and Stone comment in the first paragraph of page 586 that scattered radiation which is refracted into the capillary tube wall from the liquid core is subsequently refracted out of the fiber entirely. They assert that for such indices of refraction, the only energy that travels along the fiber is that which travels solely in the core.

Evaluating the hollow glass fiber system as a whole, it can be seen that the system may make some contributions, but it still may leave some important needs unfulfilled. It has been seen that the system increases the intensity of the scattered radiation at the collection optics in proportion to the increase in the length of the liquid filled hollow glass fiber. It has also been seen that because the operation of the system is highly dependent on the phenomenon of total internal reflection, the system may not be easily adapted to the analysis of gas samples or to the analyses of other scattering medium that have relatively low refractive indices. This leaves an important unfulfilled need for a system that operates independent of the refractive index of the scattering medium and allows for the analysis of a wide range of substances.

Because the operation of the system is highly dependent on the phenomenon of total internal reflection over an inherently limited range of acute angles less than the critical angle, the system is limited in collecting the available scattered radiation. This leaves an important unfulfilled need for a system that is constructed for collecting the available scattered radiation over a wide range of incident angles.

SUMMARY OF THE INVENTION

The present invention is primarily directed to providing an apparatus and a method that can greatly intensify weakly scattered electromagnetic radiation collected from a gas scattering medium. This is accomplished through the utilization of a reflective tubular shield that encloses the gas. A source for providing a stimulating electromagnetic radiation is coupled to the shield so that the stimulating radiation and the gas interact, producing the scattered radiation. The reflective shield is highly reflective of the scattered radiation so as to substantially contain the scattered radiation independent of the refractive index of the gas. An exit means is coupled to the shield to allow the scattered radiation to pass from containment by the shield. Through the use of the reflective shield, the scattering path length is effectively increased for a given solid angle of collection at the exit means. This in turn greatly increases the intensity of the scattered radiation collected at the exit means.

It should be understood that the term "reflective" is interpreted in the context of the present invention as relating to common reflection and excluding the special phenomenon of total internal reflection. Unlike the glass fiber system discussed previously in the background of the invention, the present invention does not rely primarily upon the phenomenon of total internal reflection. This means that the present invention is not limited to a liquid scattering medium having a high index of refraction. This also means that the present invention is not limited to total internal reflection of scattered radiation at acute angles less than the critical angle.

The shield of the present invention is highly reflective so as to substantially contain the scattered radiation independent of the optical properties of the scattering medium. For this reason, the present invention is easily adapted to the direct analysis of gas samples and to the direct analyses of other samples that happen to have relatively low refractive indices. The shield of the present invention is highly reflective of scattered radiation over a wide range of angles of incidence. This fulfills the need for a system that is constructed for collecting the available scattered radiation over a wide range of angles.

In the preferred embodiment, the reflective shield is in the form of an elongated hollow reflective tube having circular cross section. The hollow reflective tube includes a wall substantially enclosing an interior region having a longitudinal dimension. The scattering medium is substantially distributed along the longitudinal dimension of the interior region.

In the preferred embodiment, the source of stimulating radiation includes a laser that produces a laser beam. The stimulating radiation includes this laser beam. The laser is coupled to the reflective tube so that the laser beam propagates along the longitudinal dimension of the interior region, interacting with the scattering medium along a scattering region to produce the scattered radiation. Scattered radiation that radiates out from the scattering region and encounters the reflective tube is substantially contained by reflection. The scattered radiation is substantially contained by the reflective tube so that the scattered radiation propagates along the longitudinal dimension of the interior region. The use of the laser provides a relatively intense source of stimulating radiation. As a more intense stimulating source is used, this provides for the production and subsequent collection of more intense scattered radiation.

In the preferred embodiment, the exit means is coupled to the wall of the reflective tube so as to allow the scattered radiation to pass from containment by the reflective tube. The scattered radiation collected at the exit means forms an intensified image of the scattering region. This intensified image is well adapted to subsequent detection and spectral analysis. The reflective tube has two ends: a first end and an opposing end. In some alternative embodiments, the exit means is coupled to one of the two ends of the reflective tube so as to collect the scattered radiation.

Interaction between the laser beam and the reflective shield primarily produces a reflected laser beam, but a weak collateral radiation is also produced. This weak collateral radiation is unwanted because it tends to interfere with measurements of the scattered radiation. In the preferred embodiment, the laser beam propagates along the longitudinal dimension of the interior region without contacting the reflective shield. This allows for interaction between the laser beam and the scattering medium so as to produce the scattered radiation, while limiting the production of unwanted collateral radiation.

In some alternative embodiments, the reflective shield further includes a first end cap coupled to the first end of the reflective tube. The first end cap is in optical communication with the laser in such a way that the laser beam propagating along the longitudinal dimension of the interior region substantially reaches the first end cap. The first end cap is substantially reflective of the laser beam so as to reintroduce the laser beam to propagation along the longitudinal dimension of the interior region. This reintroduction of the laser beam by the first end cap causes more scattered radiation to be produced and intensifies the scattered radiation collected at the exit means. The first end cap is substantially reflective of the scattered radiation so as to reintroduce the scattered radiation to propagation along the longitudinal dimension of the interior region. This reintroduction of the scattered radiation by the first end cap further intensifies the scattered radiation collected at the exit means.

In some alternative embodiments, the shield includes the first end cap coupled to the first end of the reflective tube, and also includes a second end cap coupled to the opposing end of the reflective tube. The operation of the first end cap is generally the same as previously discussed. The second end cap is in optical communication with first end cap in such a way that the laser beam substantially reflected by the first end cap substantially reaches the second end cap. The second end cap is substantially reflective of the laser beam so as to reintroduce the laser beam to propagation along the longitudinal dimension of the interior region. This reintroduction of the laser beam by the second end cap causes more scattered radiation to be produced and further intensifies the scattered radiation collected at the exit means. The second end cap is substantially reflective of the scattered radiation so as to reintroduce the scattered radiation to propagation along the longitudinal dimension of the interior region. This reintroduction of the scattered radiation by the second end cap further intensifies the scattered radiation collected at the exit means. In other alternative embodiments, the first and second end cap discussed are in optical communication so as to form and optical resonant cavity for the laser beam. Such an optical resonant cavity is an external resonant cavity for the laser.

Yet another alternative embodiment includes the pair of end caps, the reflective tube enclosing the scattering medium, and an optical gain means such as a Helium-Neon plasma tube. The plasma tube and the reflective tube are coupled to each other and are coupled between the pair of end caps. The plasma tube and the pair of end caps are in optical communication so as to produce a laser beam. The laser beam optically resonates between the pair of end caps while passing through the plasma tube and the scattering medium. The pair of end caps form a primary cavity for the laser beam. The laser beam is especially intense within this primary cavity. As discussed previously, the scattering medium and the laser beam interact to produce the weakly scattered radiation. Since the laser beam is especially intense, more intense scattered radiation is collected at the exit means coupled to the reflective tube.

In the preferred embodiment, the reflective shield means also includes a hollow dielectric tube that is substantially transparent to the scattered radiation at a wave length of the scattered radiation. The dielectric tube has an outer surface that is optically smooth at the wave length of the scattered radiation. The reflective tube is a sheathing substantially covering the outer surface of the dielectric tube. The purpose of the dielectric tube is to provide structural support and the optically smooth outer surface for the reflective tube. The dielectric tube also protects the reflective tube from contact with the scattering medium.

At particular wavelengths of the scattered radiation, small losses occur when scattered radiation travels through the dielectric material of the hollow dielectric tube to be reflected by the reflective tube. In an alternative embodiment, the sheathing is deposited so that it substantially covers an inner surface of the hollow dielectric tube. The inner surface of the hollow dielectric tube is optically smooth at the wave length of the scattered radiation. This alternative embodiment does not protect the reflective tube from contact with the scattering medium as discussed previously. However, this alternative embodiment does limit the small losses that occur when scattered radiation travels through the dielectric material of the dielectric tube.

An appreciation of other aims and objectives of the present invention and a more complete and comprehensive understanding of this invention may be achieved by studying the following description of various embodiments and by referring to the accompanying drawings.

DETAILED DESCRIPTION OF THE INVENTION

Figure 1:
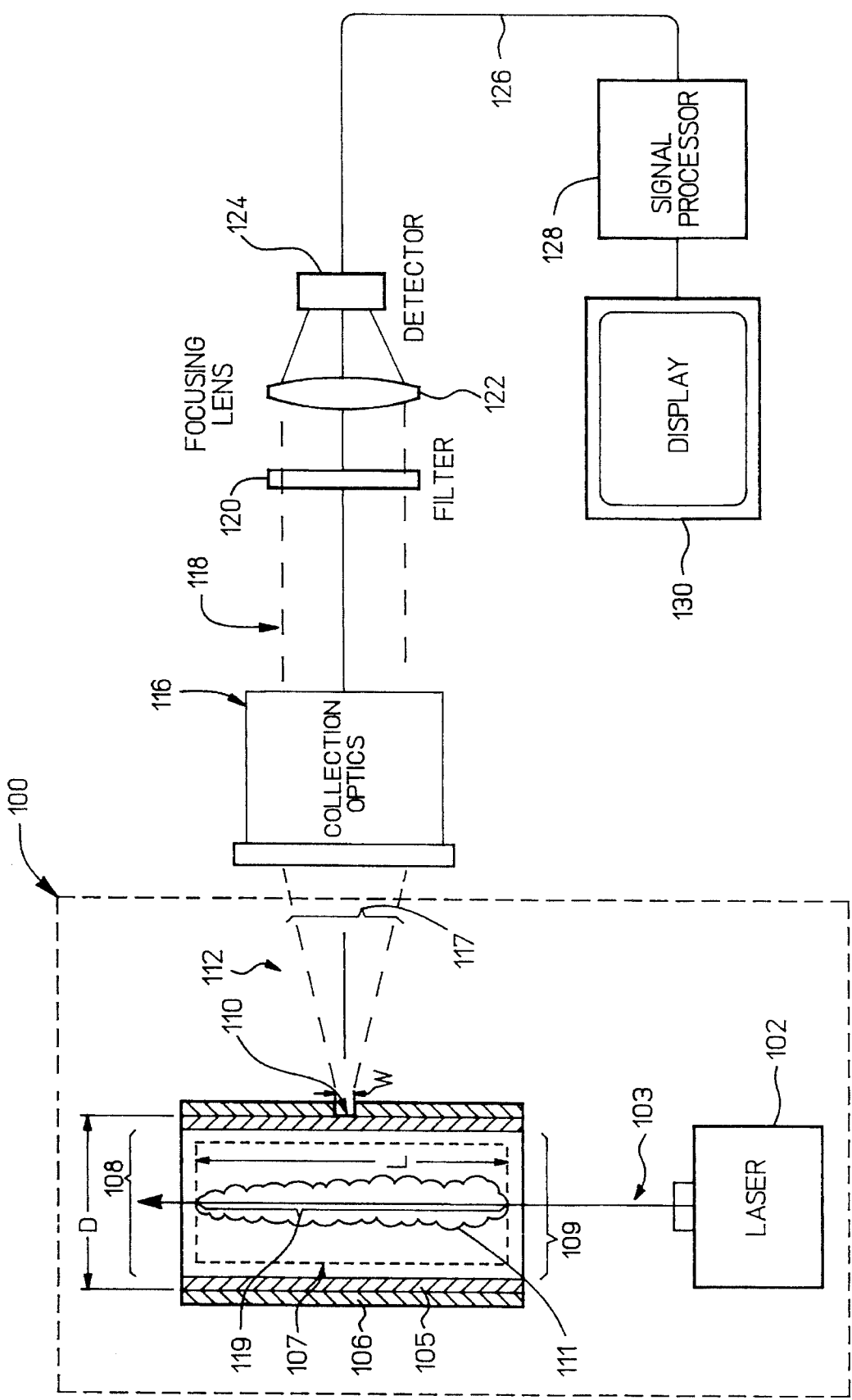
FIG. 1 is a schematic diagram illustrating a preferred embodiment of the present invention used in conjunction with conventional spectrometric collection optics and detection components.

As shown in the drawings for purposes of illustration, the invention is embodied in a reflective tubular shield means enclosing a scattering medium. A source for providing a stimulating electromagnetic radiation is coupled to the shield means so that the stimulating radiation and the scattering medium interact, producing the scattered radiation. The reflective shield is highly reflective of the scattered radiation so as to substantially contain the scattered radiation independent of the refractive index of the scattering medium. An exit means is coupled to the shield means to allow the scattered radiation to pass from containment by the shield means.

Through the use of the reflective shield means, the intensity of the scattered radiation collected at the exit means is greatly increased. Unlike the glass fiber system discussed previously in the background of the invention, the present invention does not rely primarily upon the phenomenon of total internal reflection. The present invention is easily adapted to the direct analysis of gas samples and to the direct analyses of other samples that happen to have relatively low refractive indices.

FIG. 1 is a schematic diagram illustrating the preferred embodiment of the present invention 100 used in conjunction with collection optics 116 and a detection system. The reflective shield means includes a hollow reflective tube 106 that has a circular cross section. The reflective tube has two ends: a first end 108 and an opposing end 109. The reflective tube includes a wall that substantially encloses an interior region 107 having a longitudinal dimension L. In the preferred embodiment, gasses 111 exhaled by a surgical patient under anesthesia are used as a scattering medium 111. The gasses have optical properties including low refractive indices. The gasses 111 are substantially distributed along the longitudinal dimension of the interior region.

A source of stimulating radiation includes a Helium Neon laser 102 that produces a laser beam 103. The laser is coupled to the reflective tube so that the laser beam enters the reflective tube through an inlet aperture in the opposing end 109 of the reflective tube. The laser beam propagates along the longitudinal dimension of the interior region 107 without contacting the reflective tube 106. This allows the laser beam to interact with gasses 111 along a scattering region 119. The interaction of the laser beam 103 and scattering medium 111 produces a weakly scattered electromagnetic radiation. The laser beam exits the reflective tube through an outlet aperture in the first end 108 of the reflective tube. Within practical limits, it is desirable to increase the longitudinal dimension L so as produce more scattered radiation. In the preferred embodiment, the longitudinal dimension L is approximately 100 millimeters long.

The reflective shield means also includes a hollow dielectric tube 105 that is substantially transparent to the scattered radiation at a wave length of the scattered radiation. In the preferred embodiment the dielectric tube 105 is a glass tube 105. The glass tube has an outer surface that is optically smooth at the wave length of the scattered radiation. The reflective tube 106 is a sheathing substantially covering the outer surface of the glass tube 105.

The reflective tube is highly reflective of the scattered radiation independent of the optical properties of the scattering medium 111. For example, the reflective tube is highly reflective of the scattered radiation independent of the low refractive indices of the gasses 111. Scattered radiation that radiates out from the scattering region 119, and encounters the reflective tube is substantially contained by reflection. The scattered radiation contained by the reflective tube propagates along the longitudinal dimension of the interior region 107. The exit means 110 allows the scattered radiation 112 to pass from containment by the reflective tube 106.

The exit means includes a wall aperture 110. The wall aperture 110 is a small region of the outer surface of the glass tube 105 that is not covered by the reflective tube 106. The wall aperture 110 images sections of the scattering region 119 onto collection optics 116 that are aligned with the wall aperture 110 to collect the scattered radiation 112. In the preferred embodiment, the wall aperture is a rectangular semiband. The length of the rectangular semiband wraps half way around the circumference of glass tube 105. The width W of the rectangular semi-band is determined according to the inner diameter D of the reflective tube and according to the requirements imposed by the collection optics. In the preferred embodiment the reflective tube has an inner diameter D of approximately 2.2 millimeters and the collection optics selected have an f/-number of approximately f/1. The width W of the rectangular semiband is approximately 0.6 millimeters. The rectangular shape of the wall aperture is well adapted for imaging the scattered radiation 112 onto a slit of a spectrometer detector 124. However, it is also known that circular shaped apertures have other benefits when collecting light with conventional circular lenses.

The scattered radiation 112 collected at the wall aperture 110 forms an intensified image 117 of the scattering region. The intensified image 117 includes: a direct image of a first section of the scattering region, and a plurality of reflected images corresponding to a plurality of remaining sections of the scattering region. The inner diameter D of the reflective tube is sufficiently larger than the narrow diameter of the laser beam so as to substantially improve quality of the intensified image 117. The quality of the intensified image 117 is also substantially improved by locating the aperture 110 at a position approximately adjacent to a midpoint of the longitudinal dimension L of the interior region.

The invention 100 may be used in conjunction with conventional spectrometric devices to provide a reliable and rapid determination of the presence and concentration of the gasses 111 exhaled by the surgical patient under anesthesia. The intensified image 117 is gathered by the collection optics assembly 116. The collection optics transform the intensified image 117 into a collimated image 118. From the collection optics 116, the collimated image 118 then passes through a filter 120, a focusing lens 122, and is then imaged onto a detector 124. The detector 124 transforms the collimated image 118 into electrical signals which are processed in the signal processor 128 and then displayed on the display 130.

Alternative Embodiments

Figure 2:
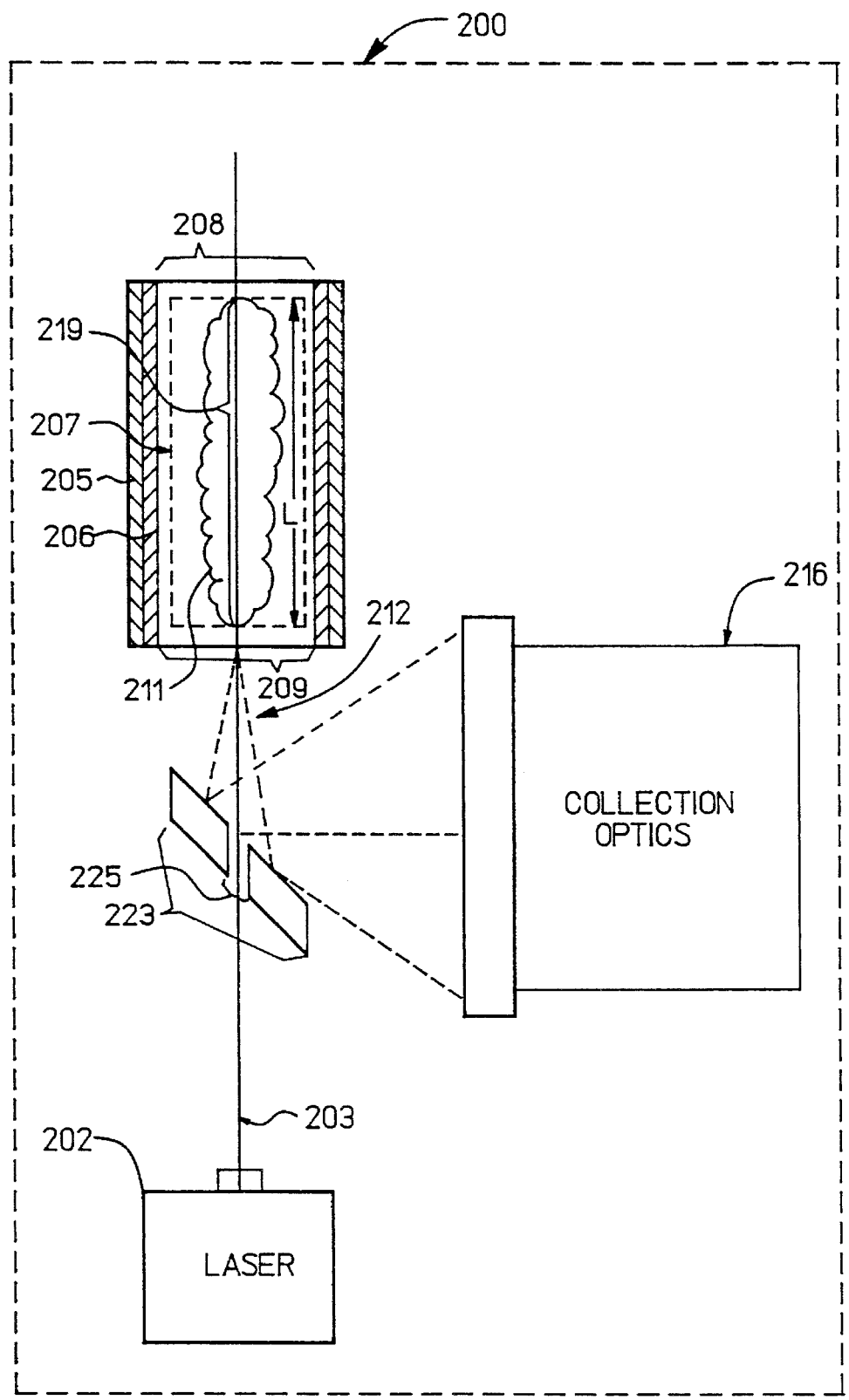
FIG. 2 Is a schematic diagram illustrating a first alternative embodiment of the present invention.

FIG. 2 is a schematic diagram illustrating a first alternative embodiment of the present invention 200 used in conjunction with collection optics 216. A reflective shield means includes a hollow reflective tube 206 that has a circular cross section. The reflective tube has two ends: a first end 208 and an opposing end 209. The reflective tube has a wall substantially enclosing an interior region 207. The interior region 207 has a longitudinal dimension L. A scattering medium 211 is substantially distributed along the longitudinal dimension of the interior region. The scattering medium has optical properties, including a refractive index.

A source of stimulating radiation includes a laser 202 that produces a laser beam 203. The laser is coupled to the reflective tube so that the laser beam enters the reflective tube through an inlet aperture in the opposing end 209 of the reflective tube. The laser beam propagates along the longitudinal dimension of the interior region 207. This allows the laser beam to interact with the scattering medium 211 along a scattering region 219. The interaction of the laser beam 203 and scattering medium 211 produces a weakly scattered electromagnetic radiation. The laser beam exits the reflective tube through an outlet aperture in the first end 208 of the reflective tube.

The reflective shield means also includes a hollow dielectric tube 205. The dielectric tube has an inner surface that is optically smooth at the wave length of the scattered radiation. The reflective tube 206 is a sheathing substantially covering the inner surface of the dielectric tube 205.

The reflective tube is highly reflective of the scattered radiation independent of optical properties of the scattering medium 211. Accordingly, scattered radiation that radiates out from the scattering region 219, and encounters the reflective tube is substantially contained by reflection. The scattered radiation contained by the reflective tube propagates along the longitudinal dimension of the interior region 207.

An exit means is coupled to the opposing end so as to allow the scattered radiation 212 to pass from containment by the reflective tube 206. The exit means includes the inlet aperture in the opposing end 209 of the reflective tube. The size of the inlet aperture roughly corresponds to the size of the circular cross section of the reflective tube, effectively making the reflective tube open ended at the opposing end. The exit means further includes a reflective block 223. The reflective block is aligned with the inlet aperture and is aligned with the collection optics 216 so as to substantially reflect the scattered radiation 212 from the inlet aperture into the collection optics. The reflective block 223 has a block aperture 225. The block aperture is aligned with the laser 202 so as to allow the laser beam 203 to pass through the block aperture 225 without contacting the reflective block 223.

Figure 3:
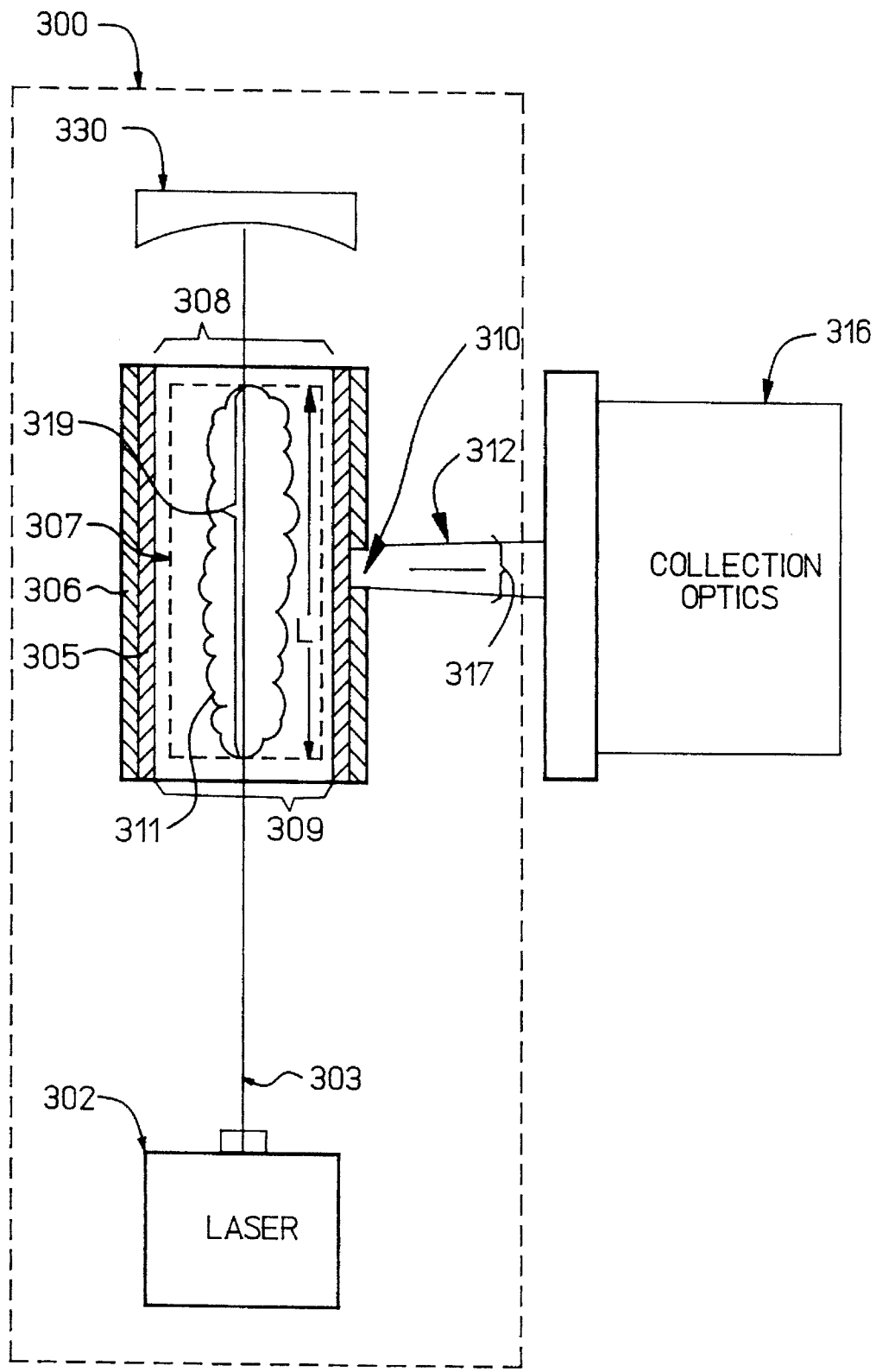
FIG. 3 is a schematic diagram illustrating a second alternative embodiment of the present invention.

FIG. 3 is a schematic diagram illustrating a second alternative embodiment of the present invention 300 used in conjunction with collection optics 316. A reflective shield means includes a hollow reflective tube 306. The reflective tube has two ends: a first end 308 and an opposing end 309. The reflective tube includes a wall that substantially encloses an interior region 307 having a longitudinal dimension L. A scattering medium 311 is substantially distributed along the longitudinal dimension of the interior region.

A source of stimulating radiation includes a laser 302 that produces a laser beam 303. The laser is coupled to the reflective tube so that the laser beam enters the reflective tube through an inlet aperture in the opposing end 309 of the reflective tube. The laser beam propagates along the longitudinal dimension of the interior region 307. This allows the laser beam to interact with the scattering medium 311 along a scattering region 319. The interaction of the laser beam 303 and scattering medium 311 produces a weakly scattered electromagnetic radiation. The laser beam exits the reflective tube through an outlet aperture in the first end 308 of the reflective tube.

The reflective shield means further includes a first end cap 330. The first end cap 330 is aligned with the laser 302 so that the laser beam 303 encounters the first end cap after the laser beam exits the first end 308 of the reflective tube. As shown in FIG. 3, the first end cap is in optical communication with the laser so that the laser beam 303 travels along an incident path and substantially reaches the first end cap. The first end cap substantially reflects the laser beam so as to cause the laser beam to retrace the incident path. Accordingly, the laser beam reenters the reflective tube through the outlet aperture in the first end of the reflective tube. Upon reentering the reflective tube, the laser beam is reintroduced to propagation along the longitudinal dimension of the interior region. The laser beam again interacts with the scattering medium along the scattering region, thereby producing more scattered radiation.

The reflective shield means also includes a hollow dielectric tube 305 that is substantially transparent to the scattered radiation at a wave length of the scattered radiation. The dielectric tube has an outer surface that is optically smooth at the wave length of the scattered radiation. The reflective tube 306 is a sheathing substantially covering the outer surface of the dielectric tube 305.

The reflective tube is highly reflective of the scattered radiation independent of optical properties of the scattering medium 311. Scattered radiation that radiates out from the scattering region 319, and encounters the reflective tube is substantially contained by reflection. The scattered radiation contained by the reflective tube propagates along the longitudinal dimension of the interior region 307, substantially reaching the first end cap 330. The first end cap is substantially reflective of the scattered radiation so as to reintroduce the scattered radiation to propagation along the longitudinal dimension of the interior region.

The exit means 310 allows the scattered radiation 312 to pass from containment by the reflective tube 306. The exit means includes a wall aperture 310. The wall aperture 310 is a small region of the outer surface of the glass tube 305 that is not covered by the reflective tube 306. The wall aperture 310 images sections of the scattering region 319 onto collection optics 316 that are aligned with the wall aperture 310 to collect the scattered radiation 312. The scattered radiation 312 collected at the wall aperture 310 forms an intensified image 317 of the scattering region.

Figure 4:
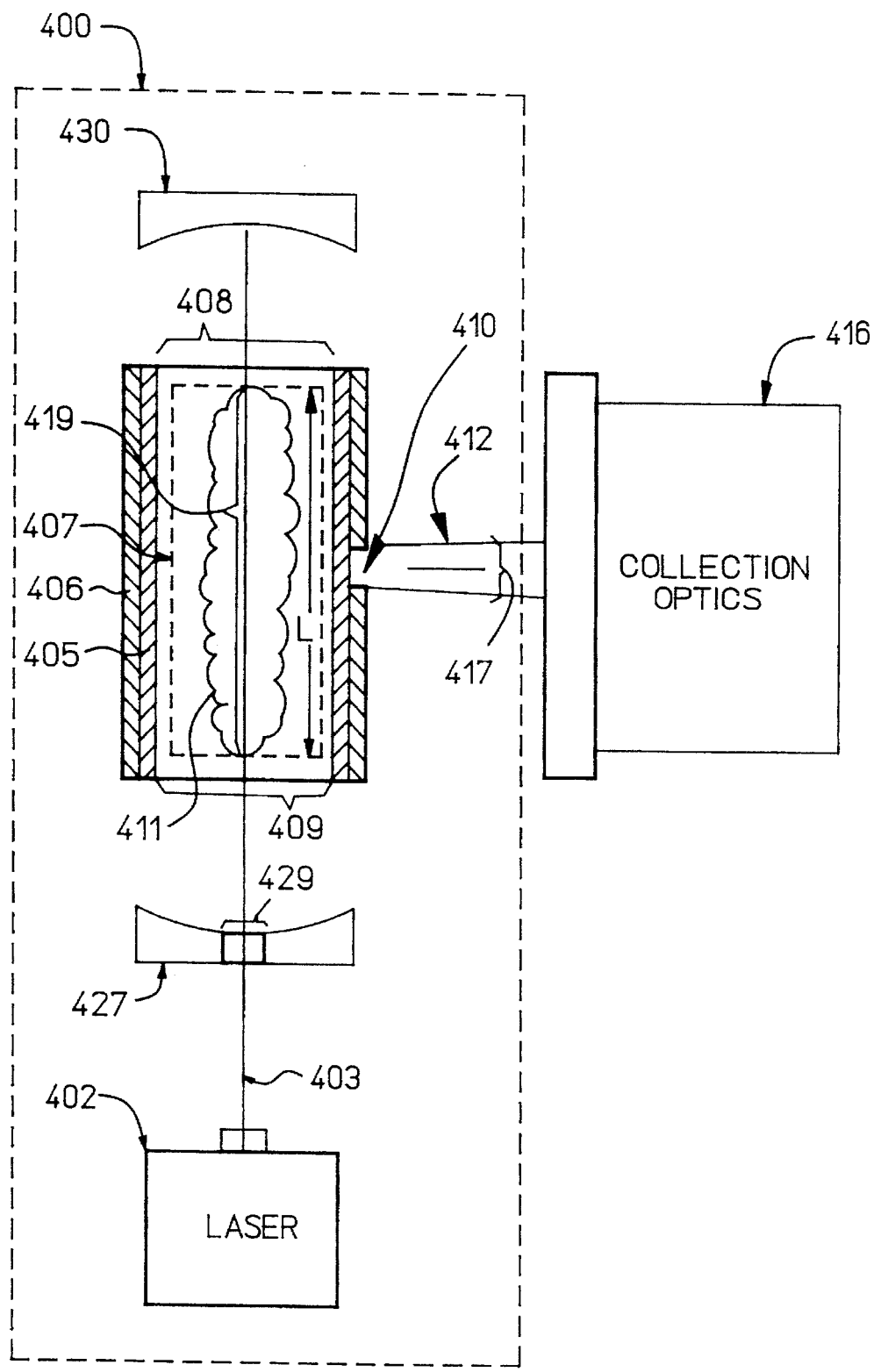
FIG. 4 is a schematic diagram illustrating a third alternative embodiment of the present invention.

FIG. 4 is a schematic diagram illustrating a third alternative embodiment of the present invention 400 used in conjunction with collection optics 416. A reflective shield means includes a hollow reflective tube 406. The reflective tube includes a wall that substantially encloses an interior region 407 having a longitudinal dimension L. A scattering medium 411 is substantially distributed along the longitudinal dimension of the interior region.

The reflective tube has two ends: a first end 408 and an opposing end 409. The reflective shield means further includes a first end cap 430 and a second end cap 427. The first end cap is coupled to the first end of the reflective tube and the second end cap is coupled to the opposing end of the reflective tube. The second end cap has a partially reflecting region 429. Such partially reflecting regions are well known to those with ordinary skill in the art of lasers.

A source of stimulating radiation includes a laser 402 that produces a laser beam 403. The laser beam travels from the laser to encounter the partially reflecting region 429 of the second end cap. The laser beam from the laser is partially transmitted through the partially reflecting region. As explained herein, the laser beam follows an initial path from the second end cap to the first end cap. Specifically, from the second end cap the laser beam then enters the reflective tube through an inlet aperture in the opposing end 409 of the reflective tube. The laser beam propagates along the longitudinal dimension of the interior region 407. This allows the laser beam to interact with the scattering medium 411 along a scattering region 419. The interaction of the laser beam 403 and scattering medium 411 produces a weakly scattered electromagnetic radiation. The laser beam exits the reflective tube through an outlet aperture in the first end 408 of the reflective tube. The first end cap 430 is aligned with the laser 402 so that the laser beam 403 substantially reaches the first end cap after the laser beam exits the first end 408 of the reflective tube.

The first end cap and the second end cap form an optical resonant cavity for the laser beam such that laser beam resonates back and forth along the initial path. Accordingly, upon reaching the first end cap, the laser beam is substantially reflected by the first end cap so that the laser beam retraces along the initial path back to the partially reflective region of the second end cap. Upon reaching the partially reflective region of the second end cap, the laser beam is substantially reflected by the second end cap so that the laser beam retraces along the initial path back to the first end cap. As the laser beam resonates back and forth along the initial path, the laser beam interacts with the scattering medium along the scattering region, producing more of the scattered radiation.

The reflective shield means also includes a hollow dielectric tube 405 that is substantially transparent to the scattered radiation at a wave length of the scattered radiation. The dielectric tube has an outer surface that is optically smooth at the wave length of the scattered radiation. The reflective tube 406 is a sheathing substantially covering the outer surface of the dielectric tube 405.

The reflective tube is highly reflective of the scattered radiation independent of optical properties of the scattering medium 411. Scattered radiation that radiates out from the scattering region 419, and encounters the reflective tube is substantially contained by reflection. The scattered radiation contained by the reflective tube propagates along the longitudinal dimension of the interior region 407, substantially reaching the first end cap 430. The first end cap and the second end cap are each substantially reflective of the scattered radiation so as to reintroduce the scattered radiation to propagation along the longitudinal dimension of the interior region.

The exit means 410 allows the scattered radiation 412 to pass from containment by the reflective tube 406. The exit means includes a wall aperture 410. The wall aperture 410 is a small region of the outer surface of the glass tube 405 that is not covered by the reflective tube 406. The wall aperture 410 images sections of the scattering region 419 onto collection optics 416 that are aligned with the wall aperture 410 to collect the scattered radiation 412. The scattered radiation 412 collected at the wall aperture 410 forms an intensified image 417 of the scattering region.

Figure 5:
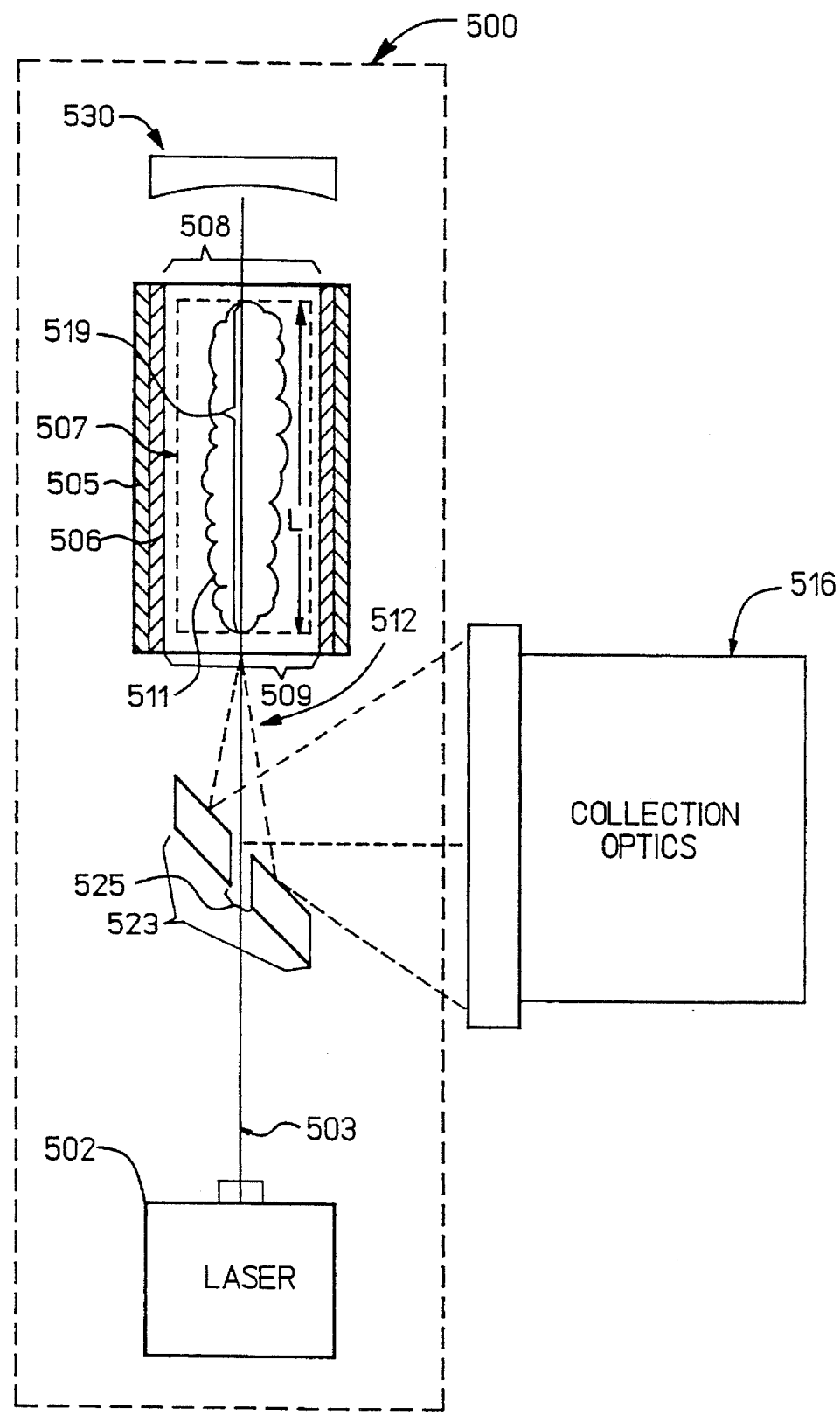
FIG. 5 is a schematic diagram illustrating a fourth alternative embodiment of the present invention.

FIG. 5 is a schematic diagram illustrating a fourth alternative embodiment of the present invention 500 used in conjunction with collection optics 516. A reflective shield means includes a hollow reflective tube 506 that has a circular cross section. The reflective tube has two ends: a first end 508 and an opposing end 509. The reflective tube has a wall substantially enclosing an interior region 507. The interior region 507 has a longitudinal dimension L. A scattering medium 511 is substantially distributed along the longitudinal dimension of the interior region. The scattering medium has optical properties, including a refractive index.

A source of stimulating radiation includes a laser 502 that produces a laser beam 503. The laser is coupled to the reflective tube so that the laser beam enters the reflective tube through an inlet aperture in the opposing end 509 of the reflective tube. The laser beam propagates along the longitudinal dimension of the interior region 507. This allows the laser beam to interact with the scattering medium 511 along a scattering region 519. The interaction of the laser beam 503 and scattering medium 511 produces a weakly scattered electromagnetic radiation. The laser beam exits the reflective tube through an outlet aperture in the first end 508 of the reflective tube.

The reflective shield means further includes a first end cap 530. The first end cap 530 is aligned with the laser 502 so that the laser beam 503 encounters the first end cap after the laser beam exits the first end 508 of the reflective tube. As shown in FIG. 5, the first end cap is in optical communication with the laser so that the laser beam 503 travels along an incident path and substantially reaches the first end cap. The first end cap substantially reflects the laser beam so as to cause the laser beam to retrace the incident path. Accordingly, the laser beam reenters the reflective tube through the outlet aperture in the first end of the reflective tube. Upon reentering the reflective tube, the laser beam is reintroduced to propagation along the longitudinal dimension of the interior region. The laser beam again interacts with the scattering medium along the scattering region, thereby producing more scattered radiation.

The reflective shield means also includes a hollow dielectric tube 505. The dielectric tube has an inner surface that is optically smooth at the wave length of the scattered radiation. The reflective tube 506 is a sheathing substantially covering the inner surface of the dielectric tube 505.

The reflective tube is highly reflective of the scattered radiation independent of optical properties of the scattering medium 511. Accordingly, scattered radiation that radiates out from the scattering region 519, and encounters the reflective tube is substantially contained by reflection. The scattered radiation contained by the reflective tube propagates along the longitudinal dimension of the interior region 507.

An exit means is coupled to the opposing end so as to allow the scattered radiation 512 to pass from containment by the reflective tube 506. The exit means includes the inlet aperture in the opposing end 509 of the reflective tube. The size of the inlet aperture roughly corresponds to the size of the circular cross section of the reflective tube, effectively making the reflective tube open at the opposing end. The exit means further includes a reflective block 523. The reflective block is aligned with the tube aperture 510 and is aligned with the collection optics 516 so as to substantially reflect the scattered radiation 512 from the tube aperture into the collection optics. The reflective block 523 has a block aperture 525. The block aperture is aligned with the laser 502 so as to allow the laser beam 503 to pass through the block aperture 525 without contacting the reflective block 523.

Figure 6:
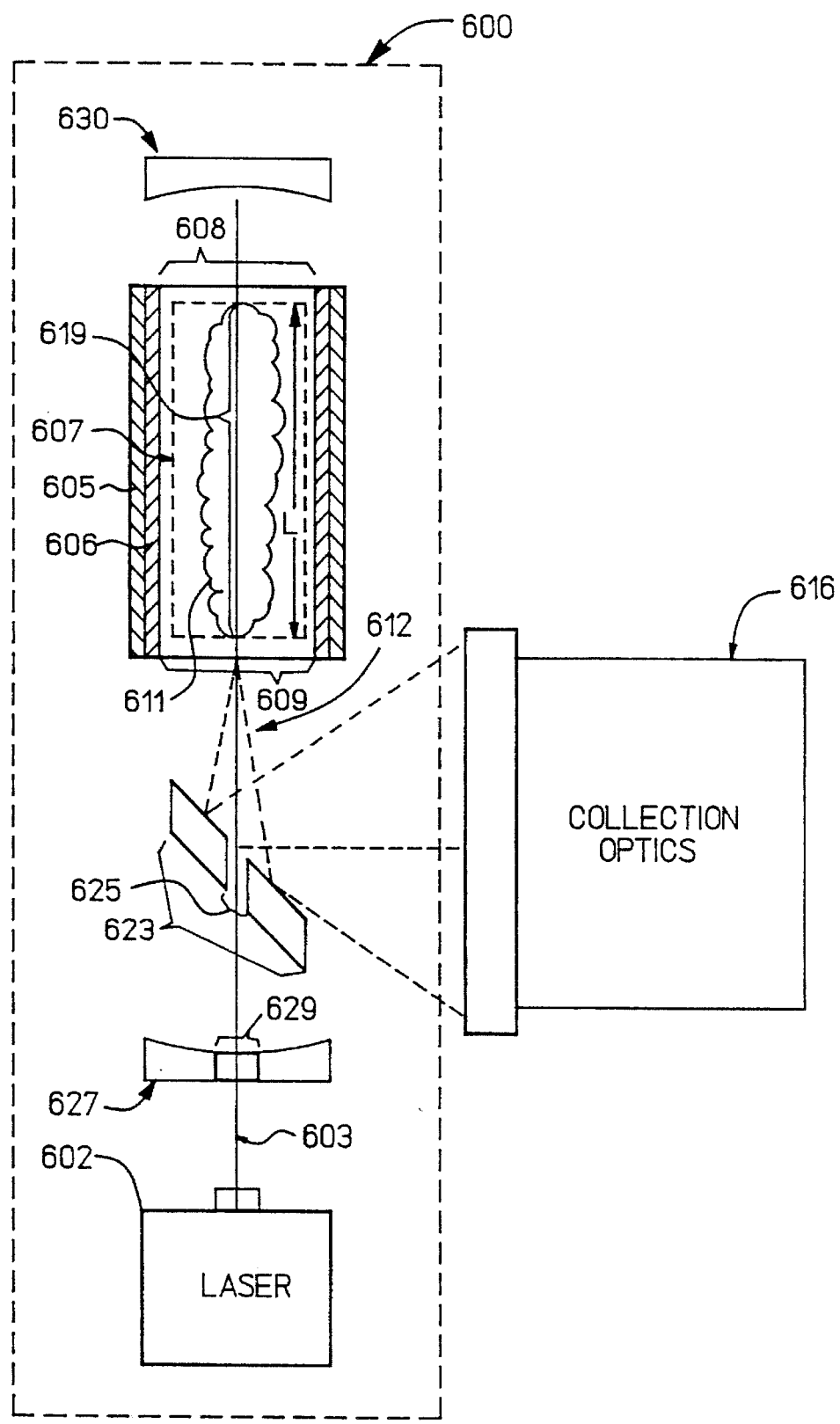
FIG. 6 is a schematic diagram illustrating a fifth alternative embodiment of the present invention.

FIG. 6 is a schematic diagram illustrating a fifth alternative embodiment of the present invention 600 used in conjunction with collection optics 616. A reflective shield means includes a hollow reflective tube 606 that has a circular cross section. The reflective tube has a wall substantially enclosing an interior region 607. The interior region 607 has a longitudinal dimension L. A scattering medium 611 is substantially distributed along the longitudinal dimension of the interior region.

The reflective tube has two ends: a first end 608 and an opposing end 609. The reflective shield means further includes a first end cap 630 and a second end cap 627. The first end cap is coupled to the first end of the reflective tube and the second end cap is coupled to the opposing end of the reflective tube. The second end cap has a partially reflecting region 629. Such partially reflecting regions are well known to those with ordinary skill in the art of lasers.

A source of stimulating radiation includes a laser 602 that produces a laser beam 603. The laser beam travels from the laser to encounter the partially reflecting region 629 of the second end cap. The laser beam from the laser is partially transmitted through the partially reflecting region. As explained herein, the laser beam follows an initial path from the second end cap to the first end cap. Specifically, from the second end cap the laser beam then enters the reflective tube through an inlet aperture in the opposing end 609 of the reflective tube. The laser beam propagates along the longitudinal dimension of the interior region 607. This allows the laser beam to interact with the scattering medium 611 along a scattering region 619. The interaction of the laser beam 603 and scattering medium 611 produces a weakly scattered electromagnetic radiation. The laser beam exits the reflective tube through an outlet aperture in the first end 608 of the reflective tube. The first end cap 630 is aligned with the laser 602 so that the laser beam 603 substantially reaches the first end cap after the laser beam exits the first end 608 of the reflective tube.

The first end cap and the second end cap form an optical resonant cavity for the laser beam such that laser beam resonates back and forth along the initial path. Accordingly, upon reaching the first end cap, the laser beam is substantially reflected by the first end cap so that the laser beam retraces along the initial path back to the partially reflective region of the second end cap. Upon reaching the partially reflective region of the second end cap, the laser beam is substantially reflected by the second end cap so that the laser beam retraces along the initial path back to the first end cap. As the laser beam resonates back and forth along the initial path, the laser beam interacts with the scattering medium along the scattering region, producing more of the scattered radiation.

The reflective shield means also includes a hollow dielectric tube 605. The dielectric tube has an inner surface that is optically smooth at the wave length of the scattered radiation. The reflective tube 606 is a sheathing substantially covering the inner surface of the dielectric tube 605.

The reflective tube is highly reflective of the scattered radiation independent of optical properties of the scattering medium 611. Accordingly, scattered radiation that radiates out from the scattering region 619, and encounters the reflective tube is substantially contained by reflection. The scattered radiation contained by the reflective tube propagates along the longitudinal dimension of the interior region 607.

An exit means is coupled to the opposing end so as to allow the scattered radiation 612 to pass from containment by the reflective tube 606. The exit means includes the inlet aperture in the opposing end 609 of the reflective tube. The size of the inlet aperture roughly corresponds to the size of the circular cross section of the reflective tube, effectively making the reflective tube open at the opposing end. The exit means further includes a reflective block 623. The reflective block is aligned with the inlet aperture and is aligned with the collection optics 616 so as to substantially reflect the scattered radiation 612 from the tube aperture into the collection optics. The reflective block 623 has a block aperture 625. The block aperture is aligned with the laser 602 so as to allow the laser beam 603 to pass through the block aperture 625 without contacting the reflective block 623.

Figure 7:
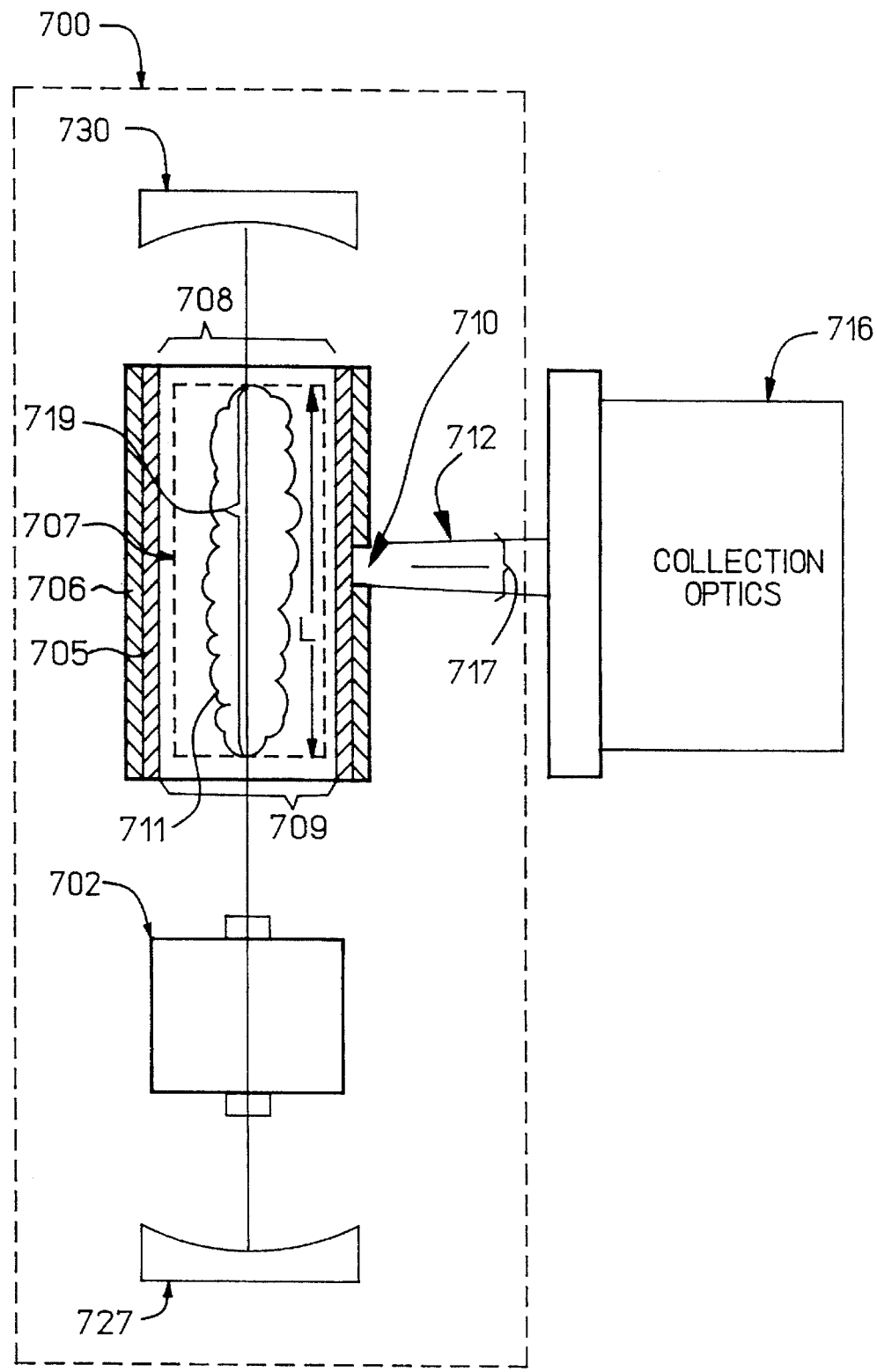
FIG. 7 is a schematic diagram illustrating a sixth alternative embodiment of the present invention.

FIG. 7 is a schematic diagram illustrating a sixth alternative embodiment of the present invention 700 used in conjunction with collection optics 716. A reflective shield means includes a hollow reflective tube 706. The reflective tube includes a wall that substantially encloses an interior region 707 having a longitudinal dimension L. A scattering medium 711 is substantially distributed along the longitudinal dimension of the interior region.

The reflective shield means further includes a pair of end caps: a first end cap 730 and a second end cap 727. As shown in FIG. 7, the reflective tube 706 is coupled to an optical gain means 702. The optical gain means 702 is a high voltage Helium-Neon plasma tube 702. The plasma tube and the reflective tube are coupled between the pair of end caps.

The first end cap and the second end cap form an optical resonant cavity for a laser beam 703 such that laser beam resonates back and forth between the first end cap and the second end cap along an initial path. The initial path is illustrated in FIG. 7 by following the laser beam 703 from the second end cap through the plasma tube 702. From the plasma tube the laser beam then enters the reflective tube through an inlet aperture in an opposing end 709 of the reflective tube. The laser beam propagates along the longitudinal dimension of the interior region 707. This allows the laser beam to interact with the scattering medium 711 along a scattering region 719. The interaction of the laser beam 703 and scattering medium 711 produces a weakly scattered electromagnetic radiation. The laser beam exits the reflective tube through an outlet aperture in a first end 708 of the reflective tube. The first end cap 730 is aligned with the laser 702 so that the laser beam 703 substantially reaches the first end cap after the laser beam exits the first end 708 of the reflective tube.

Upon reaching the first end cap, the laser beam is substantially reflected by the first end cap so that the laser beam retraces along the initial path back to the second end cap. Upon reaching the partially reflective region of the second end cap, the laser beam is substantially reflected by the second end cap so that the laser beam retraces along the initial path back to the first end cap. As the laser beam resonates back and forth along the initial path, the laser beam interacts with the scattering medium along the scattering region, producing more of the scattered radiation.

The reflective shield means also includes a hollow dielectric tube 705 that is substantially transparent to the scattered radiation at a wave length of the scattered radiation. The dielectric tube has an outer surface that is optically smooth at the wave length of the scattered radiation. The reflective tube 706 is a sheathing substantially covering the outer surface of the dielectric tube 705.

The reflective tube is highly reflective of the scattered radiation independent of optical properties of the scattering medium 711. Scattered radiation that radiates out from the scattering region 719, and encounters the reflective tube is substantially contained by reflection. The scattered radiation contained by the reflective tube propagates along the longitudinal dimension of the interior region 707, substantially reaching the first end cap 730. The first end cap and the second end cap are each substantially reflective of the scattered radiation so as to reintroduce the scattered radiation to propagation along the longitudinal dimension of the interior region.

The exit means 710 allows the scattered radiation 712 to pass from containment by the reflective tube 706. The exit means includes a wall aperture 710. The wall aperture 710 is a small region of the outer surface of the glass tube 705 that is not covered by the reflective tube 706. The wall aperture 710 images sections of the scattering region 719 onto collection optics 716 that are aligned with the wall aperture 710 to collect the scattered radiation 712. The scattered radiation 712 collected at the wall aperture 710 forms an intensified image 717 of the scattering region.

Reflective Shield Means

The reflectance of the shield means contributes greatly to the operation of the invention. In the preferred embodiment and in some alternative embodiments, a first type of shield means is used that includes a highly reflective multilayer dielectric structure. In some other alternative embodiments, a second type of shield means is used that includes a highly reflective structure made of silver. As discussed previously in the background of the invention, when electromagnetic radiation traveling in a first medium is incident upon a second medium at a particular acute angle, the load impedance presented by the second medium varies with the measure of the particular acute angle. Each of the two types of shield means present equivalent load impedances that are not purely imaginary. This means that each of the two types of shield means present equivalent load impedances that have real components. This also means that there would be an imperfect impedance mismatch between the purely real characteristic impedance of the scattering medium and each of the respective equivalent load impedances of the two shield means. Since there would not be a perfect impedance mismatch, there would not be total internal reflection of the incident radiation when each one of the two types of reflective shield means are used. Though neither of the two types of shield means would create a perfect impedance mismatch, each of two type of shield means still create an impedance mismatch that is sufficiently large so that the scattered radiation is substantially contained by reflection.

For the first type of shield means, dielectric layers are arranged to produce a multilayer dielectric structure that is highly reflective at the frequencies of the scattered radiation. The surfaces of the dielectric layers are optically smooth to incident scattered radiation so that the multilayer dielectric structure is specularly reflective at the frequencies of the scattered radiation.

Figure 8:
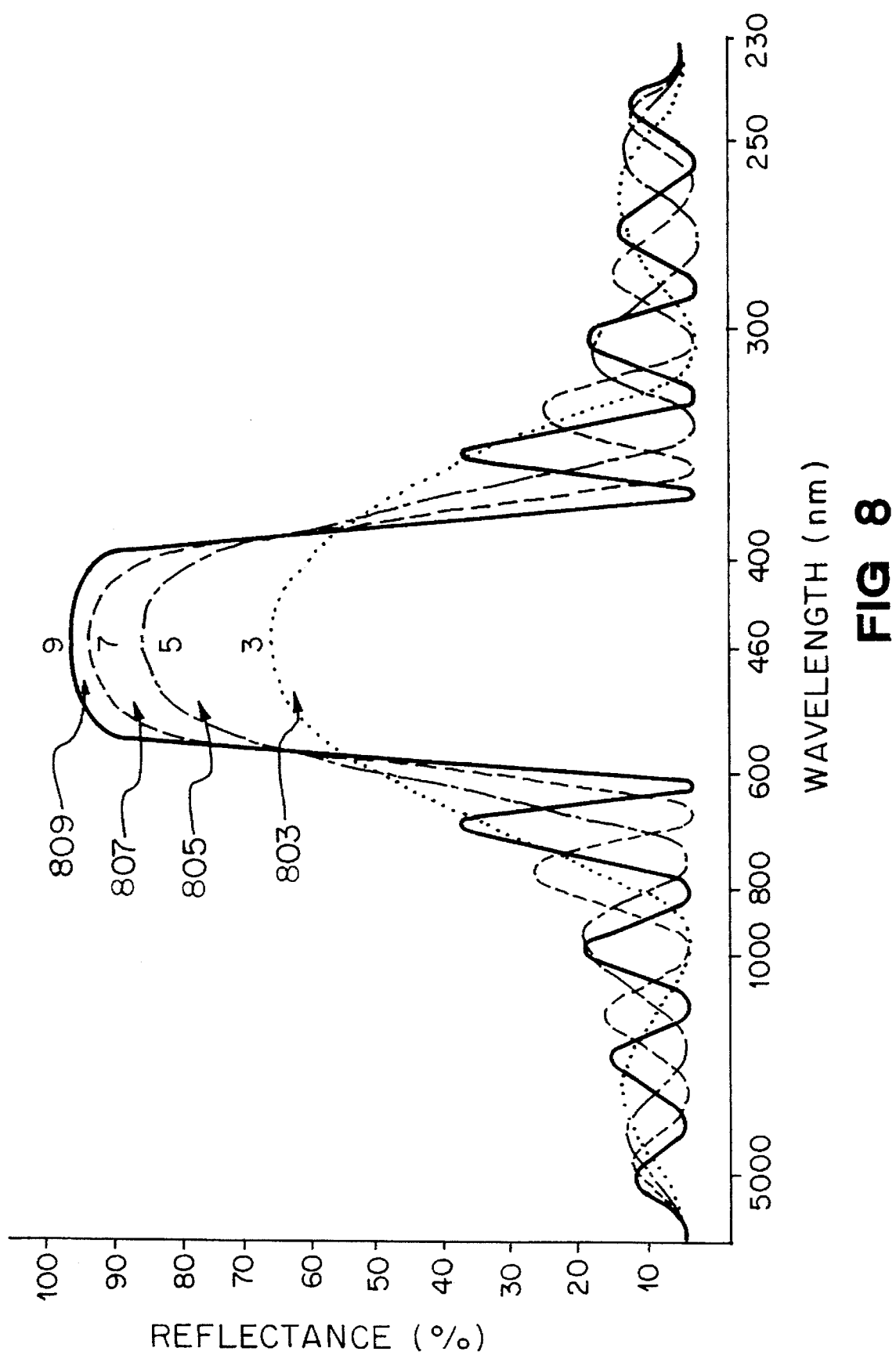
FIG. 8 is a set graph traces, each trace illustrating average reflectance of radiation normally incident on a respective multilayer dielectric structure versus frequency of the incident radiation.

For the purposes of illustration, FIG. 8 shows a graph of reflectance of normally incident radiation versus wavelength for 3 layer coatings (trace 803), 5 layer coatings (trace 805), 7 layer coatings (trace 807), and 9 layer coatings (trace 809). Such a graph is found in H. A. Macleod's "Thin Film Optical Filters" second edition, McGraw-Hill, page 167. As explained in Macleod's example, a multilayer dielectric structure is created by arranging alternating layers of two dielectric materials; one have a high refractive index and the other having a low refractive index. Macleod's example uses a high refractive index material with a refractive index of 1.52, a low refractive index material with a refractive index of 1.38. The layers of dielectric material are deposited over a transparent substrate with a refractive index of 1.52.

The conventional wisdom is to apply each layer at a thickness corresponding to one quarter of the wavelength of the radiation to be reflected. The reflection at the boundaries between layers add together constructively and this yields a peak reflectance when radiation is incident normal to each layer. Macleod's example uses such a quarter wave stack with the thickness of each layer being one quarter of the selected wavelength (one quarter of 460 nanometers). However, vendors who specialize in the application of highly reflective multilayer dielectric coatings use their own proprietary processes and the architecture of the coatings varies somewhat from a classic quarterwave stack. In the preferred embodiment, the multilayer dielectric structure is constructed so as to have a peak reflectance when the scattered radiation is incident normal to the multilayer dielectric structure. It should be understood that processes can also be used to construct a multilayer dielectric structure having a peak reflectance when scattered radiation is incident at an angle of forty five degrees (or some other angle).

Figure 10A:
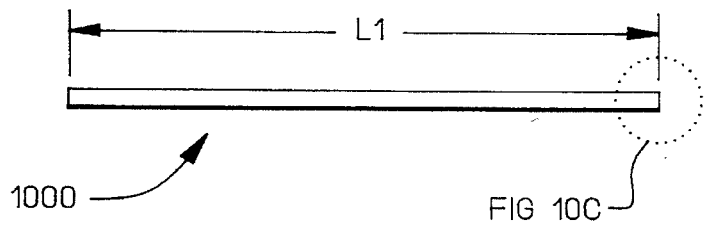
FIGS. 10A and 10B and 10C are different schematic views of the dielectric tube before it is sheathed in the reflective tube and used as part of the present invention.
Figure 10B:
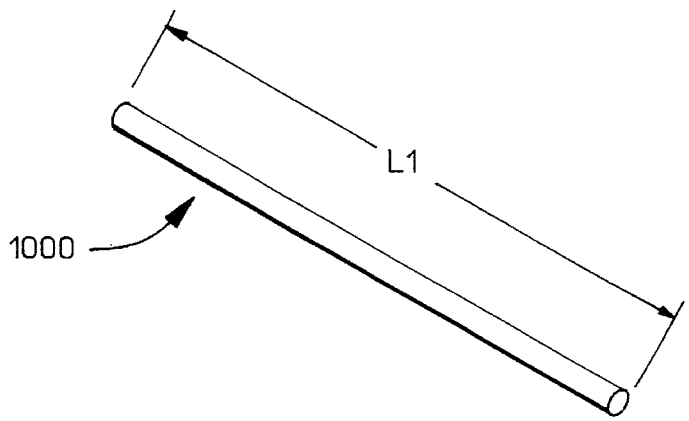
Figure 10C:
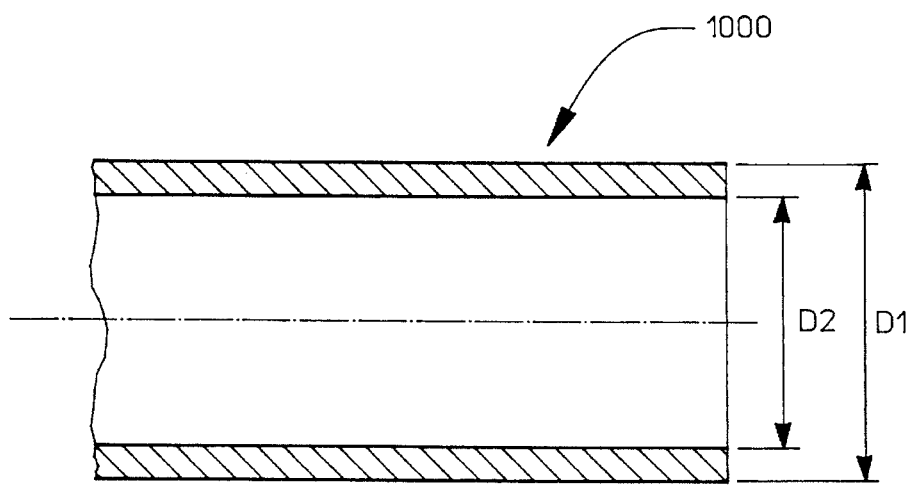

In the preferred embodiment the reflective tube is a multilayer dielectric structure that sheathes the outer surface of a hollow glass tube. The multilayer dielectric structure is constructed by depositing layers of dielectric on the outer surface of the glass tube. For the purposes of illustration, FIGS. 10A, 10B, and 10C show different views of the glass tube 1000 before the glass tube is coated. The length of the tube, L1, is approximately 100 millimeters. FIG. 10C is a cut away view of an end of the glass tube showing the outer diameter D1 and the inner diameter D2. The outer diameter, D1, is approximately 2.2 millimeters. The inner diameter, D2, is approximately 1.8 millimeters.

The dielectric layers of the multilayer dielectric structure can be deposited on the glass tube using a variety of different methods including thermal vacuum deposition, chemical vapor deposition, and sputtering. These methods are well known to those with ordinary skill in the art of optical coating. The vendor used for depositing the multilayer dielectric coatings on the outer surface of the glass tube in the preferred embodiment of the present invention is Deposition Sciences Inc. located at 386 Tesconi Court, Santa Rosa, Calif. 95401. Their telephone number is (707) 573-6700.

Figure 11A:
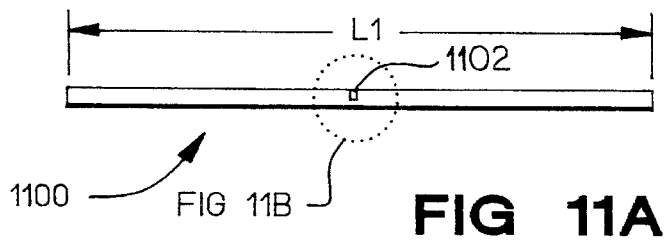
FIGS. 11A through 11E are different schematic views of the dielectric tube after it is sheathed in the reflective tube.

For the purposes of illustration, FIGS. 11A through 11E show different views of the glass tube after the exterior surface of the glass tube has been coated with layers of dielectric to form the reflective tube. As shown in FIG. 11A, the reflective tube 1100 is a sheathing substantially covering the outer surface of the glass tube. The glass tube and the reflective tube each have approximately the same length, L1, measuring approximately 100 millimeters. A wall aperture 1102 is located approximately midway along the length of the glass tube. The wall aperture 1102 is a small region of the outer surface of the glass tube that is not covered by the reflective tube 1100.

Figure 11B:
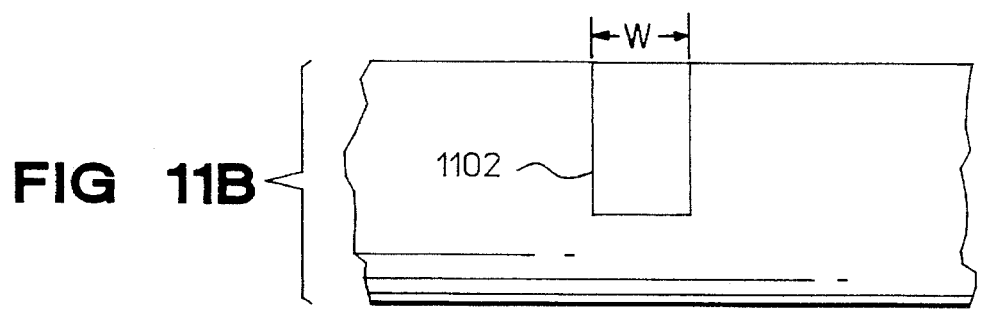
Figure 11C:
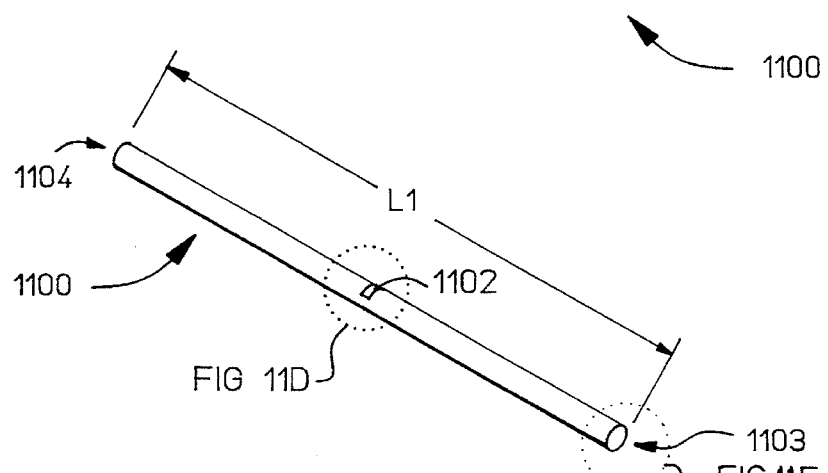
Figure 11D:
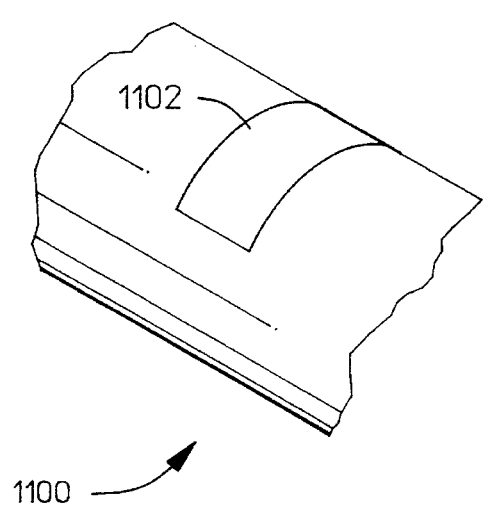

The wall aperture 1102 is a rectangular semi-band. As illustrated in FIG. 11B, the width, W, of the rectangular semiband is approximately 0.6 millimeters. FIG. 11C shows a slightly rotated view of the reflective tube 1100. FIG. 11D is a detailed rotated view of the rectangular semi-band, illustrating how the length of the rectangular semi-band wraps half way around the circumference of glass tube. The wall aperture is made by covering the small region of the outer surface of the glass tube with a masking material such as nickel alloy, before the dielectric layers are deposited on the glass tube. After the dielectric layers are deposited on the glass tube, the masking material is removed to reveal the wall aperture.

Figure 11E:
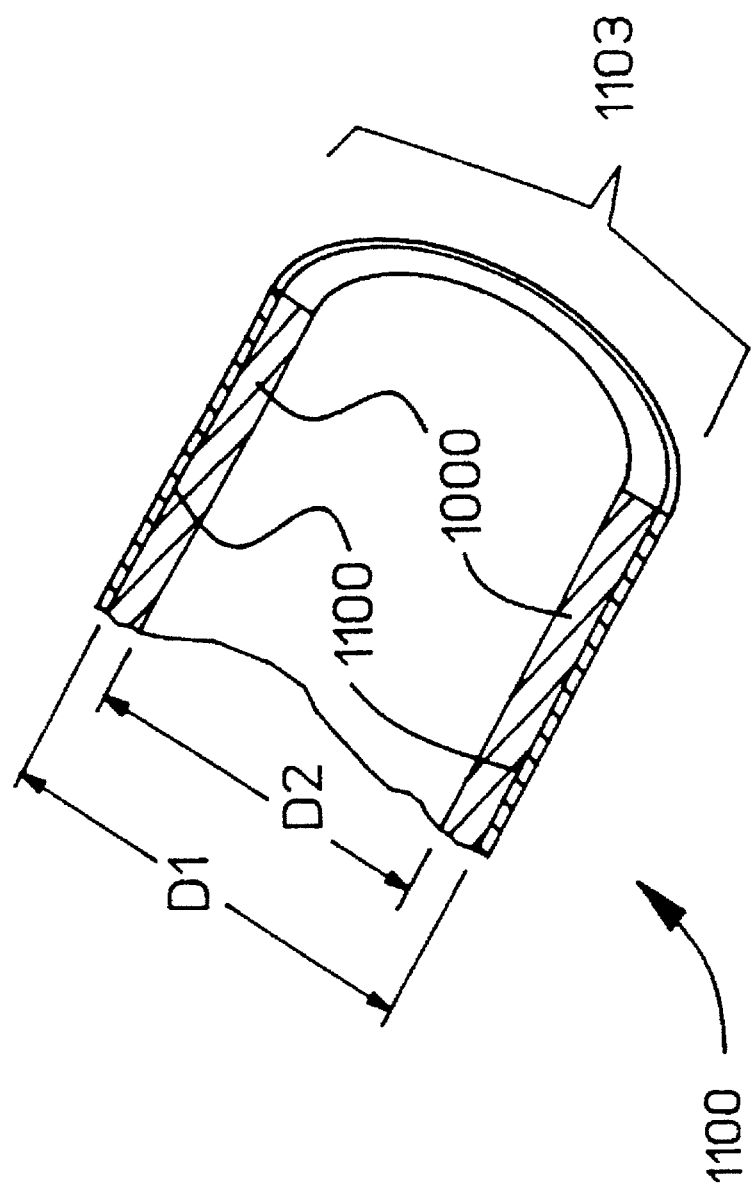

As shown by FIG. 11C, there is an inlet aperture 1103 in an opposing end of the reflective tube and an outlet aperture 1104 in a first end of the reflective tube. FIG. 11E shows a view of the opposing end of the reflective tube, cut away along the length of the glass tube and the reflective tube to show the glass tube 1000. The inlet aperture 1103 in the opposing end of the reflective tube has a size roughly corresponding to the size of the circular cross section of the reflective tube 1100, effectively making the reflective tube open ended at the opposing end. Similarly, the outlet aperture 1104 in the first end of the reflective tube effectively makes the reflective tube open ended at the first end. As shown in FIG. 11E, the glass tube has an inner diameter D2 and an outer diameter D1.

In some alternative embodiments, the reflective tube is a multilayer dielectric structure that sheathes the inner surface of a hollow glass tube. A multilayer dielectric coating can be deposited on an interior surface of a glass tube by a process of chemical vapor deposition. Chemical vapor deposition is the growth of solid films on a substrate as the result of thermochemical phase reactions. Using such a process, Deposition Sciences of Santa Rosa California can make a multilayer dielectric coating on the inner surface of glass tubes that have a moderate ratio of length to diameter.

In some alternative embodiments, the exit means includes a wall aperture in a reflective tube that sheathes the inner surface of the glass tube. The preferred method for creating a wall aperture in a reflective tube that sheathes the inner surface of the glass tube is to use a laser ablation technique. An eximer laser is directed against the outer surface of the glass tube so that the eximer laser beam refracts-through the tube and ablates the coating in the inner surface of the tube. Such eximer lasers can be purchased from Lamda Physik or other vendors.

Figure 9:
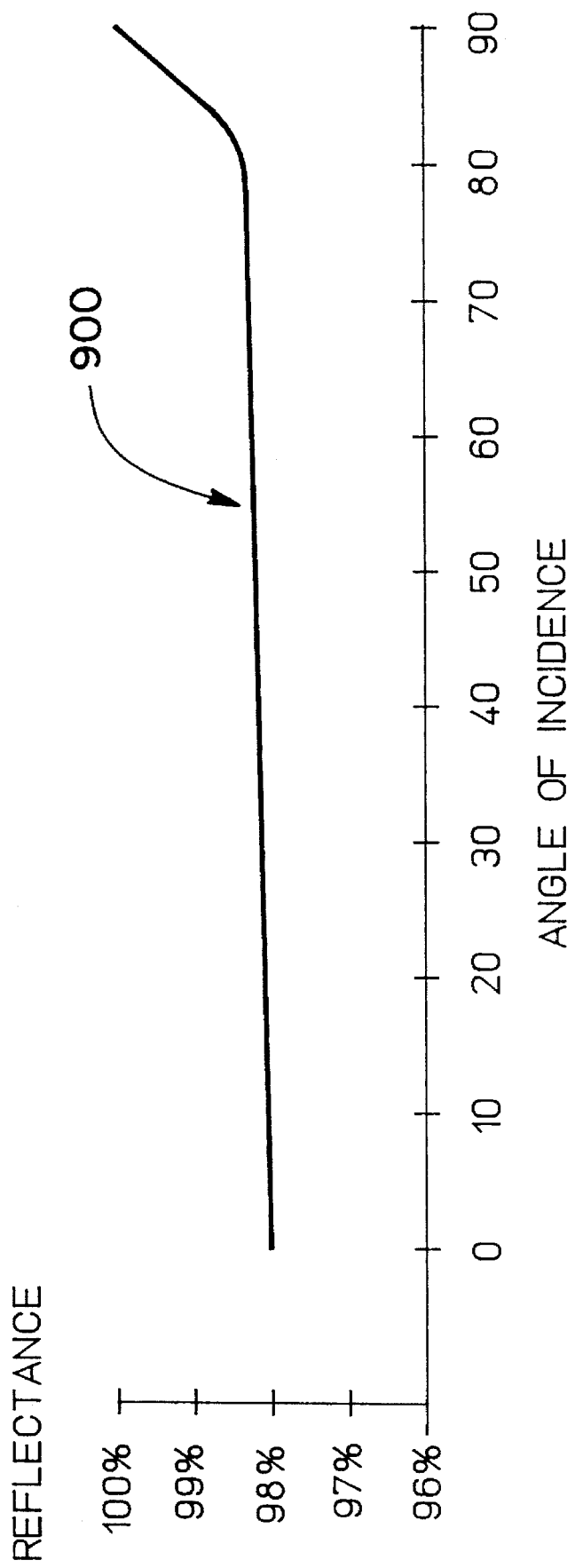
FIG. 9 is a graph showing the average reflectance of radiation incident to a silver surface over a range of angles.

Some other alternative embodiments utilize the second type of reflective shield means. Instead of a multilayer dielectric structure, this second type of shield means includes a structure made of silver. It should be understood that another metal that is highly reflective at the frequencies of interest could be used instead of silver. The surface of the silver structure is optically smooth to incident scattered radiation so that the silver structure is specularly reflective of the scattered radiation. For the purposes of illustration, FIG. 9 shows a graph of the reflectance of silver versus the angle of incident radiation (trace 900). It should be noted that reflectance of the tube is substantially improved when the thickness of the silver structure is increased in comparison to the skin depth, $\delta$, given by the equation:

$$\delta = 1/(\pi f \mu \sigma)$$

where f is the frequency of the scattered radiation, $\mu$ is the magnetic permeability of the silver, and $\sigma$ is the conductivity of the silver. For example, there is a large improvement in reflectance when the thickness of the silver structure is greater than 3 skin depths.

In some of the other alternative embodiments, the reflective tube is a silver structure that sheathes the outer surface of a hollow glass tube. The inventors have deposited silver onto the outer surface of the glass tube by using a thermal evaporation process. As an initial step of the process, a graphite crucible containing silver is placed in a chamber below the glass tube to be coated. The chamber is evacuated to $10^{-7}$ torr and the crucible is heated to vaporize the silver. Once the heating of the silver has stabilized, a shutter is opened to expose the uncoated tube to the silver vapors. The vapor condenses back to the solid state on the exposed surface of the tube, forming a uniform thin film of silver. The thickness of the silver is in the range of 0.2 to 1.0 microns.

A monitor crystal is exposed to the silver vapors at the same time so that a thin film is also deposited on the crystal. The thickness of the film is monitored during the process by observing the shift in the resonant frequency of the crystal. When the monitor crystal indicates that film is sufficiently thick, the shutter is closed to halt the exposure of the tube to the silver vapors. The glass tube is then rotated one quarter turn using its length, L1, as an axis of rotation, so that the condensing vapor forms a uniform thin film on the exterior surface of the glass tube. The thermal evaporation process is repeated again and again until all sides of the exterior surface of the tube are coated with silver. A thin layer of chromium is deposited on top of the silver by similar methods so as to protect the silver from tarnishing. The chrome layer may be approximately the same thickness as the silver layer or as little as 0.03 microns of chrome may be used with beneficial results. A vendor has also been used for depositing silver on the outer surface of the glass tube, namely CVI Laser Corporation located at 200 Dorado Place, Albuquerque, N.M. 87123. Their telephone number is (505) 296-9541.

Some alternative embodiments have a wall aperture in the silver reflective tube that sheathes the outer surface of the glass tube. Such a wall aperture is made using a razor edged knife. The razor edged knife is to used to scrape the silver off of the small region of the exterior surface of the glass tube. A low-power assembly microscope is used as a viewing aid during the scraping procedure. The small region of glass tube is then polished to achieve good optical transmission of the scattered radiation. Another way of making the wall aperture is to remove the silver from the small region by rubbing a polishing string back an forth across the small region.

In some of the other alternative embodiments, the reflective tube is a gold alloy structure that sheathes the inner surface of a hollow glass tube. A glass tube having an interior surface coated with gold alloy can be ordered from Hewlett Packard as "replacement light pipe" part number 05965-60155. This part is used in the Hewlett Packard 5965B Infrared Detector. As of the filing date of this patent application, this part is generally available for sale to the public. Some alternative embodiments have a wall aperture in the gold alloy reflective tube that sheathes the inner surface of the glass tube. Such a wall aperture can be made in the gold alloy reflective tube using the laser ablation technique discussed previously.

The system of the present invention is capable of collecting scattered light and may employ a wide range of scattering medium. Though the preferred embodiment utilizes visible light, the invention is not inherently limited to any particular band of radiation. Although the preferred embodiment utilizes Raman scattering; many other phenomena, including Raleigh, Brilluion, and Mie scattering, fluorescence and phosphorescence may be exploited with beneficial results.

Although the present invention has been described in detail with reference to a particular preferred embodiment, persons possessing ordinary skill in the art to which this invention pertains will appreciate that various modifications and enhancements may be made without departing from the spirit and scope of the claims that follow.

We claim:

1. An apparatus for collecting a weakly scattered electromagnetic radiation from a scattering medium having optical properties, comprising:

a hollow reflective tube having a wall that substantially encloses the scattering medium;

a source for providing a stimulating electromagnetic radiation; said source being coupled to the reflective tube so that the stimulating radiation and the scattering medium interact to produce the weakly scattered electromagnetic radiation; the reflective tube being highly reflective so as to substantially provide containment of the scattered radiation independent of the optical properties of the scattering medium; and reflective tube to allow the scattered radiation to pass from the containment provided by the reflective tube.

2. An apparatus as in claim 3 further comprising a hollow dielectric tube having an outer surface; the dielectric tube being substantially transparent at a wavelength of the scattered radiation and the outer surface being optically smooth at the wavelength of the scattered radiation; the reflective tube being coupled to the dielectric tube so that the reflective tube is a sheathing substantially covering the outer surface of the dielectric tube; the purpose being for the dielectric tube to provide structural support and the optically smooth outer surface for the reflective tube.

3. An apparatus as in claim 1 further comprising a hollow dielectric tube having an inner surface; the inner surface being optically smooth at a wavelength of the scattered radiation; the reflective tube being coupled to the dielectric tube so that the reflective tube is a sheathing substantially covering the inner surface of the dielectric tube; the purpose being for the dielectric tube to provide structural support, and the optically smooth inner surface for the reflective tube.

4. An apparatus for producing and collecting a weakly scattered electromagnetic radiation, comprising;

a gas having optical properties;

a reflective tube for substantially enclosing the gas;

a source for providing a stimulating electromagnetic radiation; said source being coupled to the tube so that the stimulating radiation and the gas interact, producing the weakly scattered electromagnetic radiation; the tube being highly reflective so as to substantially provide containment of the scattered radiation independent of the optical properties of the gas; and an exit means coupled to the tube for allowing the scattered radiation to pass from the containment provided by the tube.

* * * * *